United States Patent [19]
Van Gelder et al.

[11] 3,963,718
[45] June 15, 1976

[54] TETRAHYDROPYRIMIDINES

[75] Inventors: Josephus Ludovicus Hubertus Van Gelder; Alfons Herman Margaretha Raeymaekers, both of Beerse; Leopold Frans Cornell Roevens, Rijkevorsel; Willy Joannes Van Laerhoven, Ravels, all of Belgium

[73] Assignee: Janssen Pharmaceutica, Beerse, Belgium

[22] Filed: Apr. 16, 1975

[21] Appl. No.: 568,744

Related U.S. Application Data

[62] Division of Ser. No. 499,743, Aug. 13, 1974, Pat. No. 3,925,383, which is a division of Ser. No. 313,285, Dec. 8, 1972, Pat. No. 3,865,834.

[52] U.S. Cl. ............... 260/256.4 H; 260/256.4 F; 260/256.4 N; 260/309.6; 260/309.7; 260/570.5 R; 260/570.5 P; 424/251; 424/273

[51] Int. Cl.$^2$ ........................................ C07D 239/14
[58] Field of Search ............................. 260/256.4 H

[56] References Cited
UNITED STATES PATENTS
3,822,262   6/1974   Bream et al. ................ 260/256.4 H

*Primary Examiner*—Raymond V. Rush
*Assistant Examiner*—James H. Turnipseed
*Attorney, Agent, or Firm*—Salvatore R. Conte

[57] ABSTRACT

Compounds of the class of imidazo[1,2-a]-imidazoles, imidazo[1,2-a]pyrimidines and pyrimido-[1,2-a]pyrimidines useful as central nervous system (CNS) antidepressants; and certain novel precursors therefor.

2 Claims, No Drawings

TETRAHYDROPYRIMIDINES

This is a division of application Ser. No. 499,743, filed Aug. 13, 1974, now U.S. Pat. No. 3,925,383, which in turn is a division of application Ser. No. 313,285, filed Dec. 8, 1972, now U.S. Pat. No. 3,865,836.

BACKGROUND OF THE INVENTION:

The invention pertains to the field of bicyclic imidazoles and bicyclic pyrimidines having an aryl substituent in a certain position described hereinafter. The prior art discloses certain bicyclic rings but not with the designated aryl substituent in said position. Such other compounds will be found in the following references:
1. Miller et al., J. Med. Chem., 15, (4), 415 (1972);
2. C.A. 52, 7333i (1958);
3. C.A. 52, 17281i (1958);
4. C.A. 54, 19727d (1960);
5. C.A. 52, 14701e (1958); and
6. C.A. 52, 4451 (1958).

PREFERRED EMBODIMENTS:

The novel bicyclic imidazoles and pyrimidines of this invention may be structurally represented by the following formula:

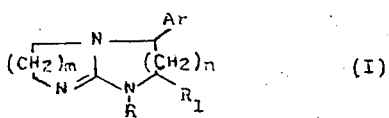

wherein
$m$ is in the integer zero or 1;
$n$ is the integer zero or 1;
R is a member selected from the group consisting of hydrogen and benzyl;
$R_1$ is a member selected from the group consisting of hydrogen and loweralkyl, preferably methyl, provided that, when said $R_1$ is loweralkyl, when said $n$ is zero; and
Ar is a member selected from the group consisting of phenyl, loweralkylphenyl, halophenyl and dihalophenyl.

The therapeutically active non-toxic acid addition salts of the foregoing compounds (I) are also embraced within the scope of this invention.

As used herein, "loweralkyl" may be straight or branch chained and have from 1 to 5 carbon atoms, such as, for example, methyl, ethyl, propyl, isopropyl, butyl, tert-butyl, pentyl and like alkyls. The preferred loweralkyl is methyl. The term "halo" refers to halogens of atomic weight less than 127, i.e., chloro, bromo, fluoro and iodo When R is hydrogen, the subject compounds (I) exhibit tautomerism due to the migration of the corresponding proton between the two nitrogens as follows:

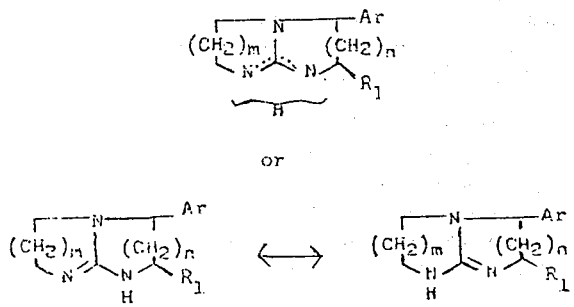

The compounds of formula (I) are conveniently prepared by ring closure of an appropriate precursor of formula (II) in which the symbols Ar, $m$, $n$, R and $R_1$ are as previously described. Such ring closure is readily accomplished by treatment with concentrated sulfuric acid or with thionyl chloride and base, e.g., sodium:

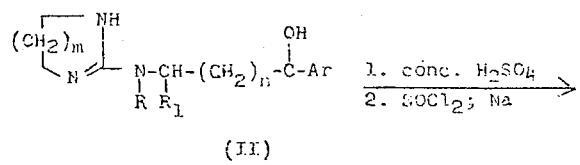

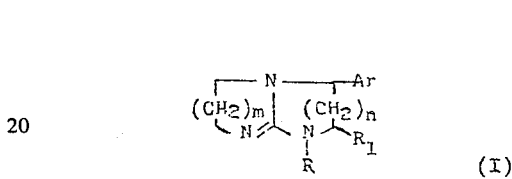

The compounds of formula (II), wherein R is hydrogen, are conveniently prepared by the reaction of an appropriate 2-nitroamino-imidazoline or 2-nitroaminotetrahydro pyrimidine of formula (III), wherein $m$ is the integer zero or 1, with an appropriate α-(aminoalkyl)benzyl alcohol of formula (IV), wherein $n$, $R_1$ and Ar are as previously defined, in a suitable inert organic solvent. Typical solvents that may be employed are aromatic hydrocarbons, e.g., benzene, toluene, xylene and the like, and ethers, e.g., dioxane and the monoethyl and diethyl ethers of ethane diol. Elevated temperatures may be employed to enhance the rate of reaction. The foregoing reactions may be illustrated as follows:

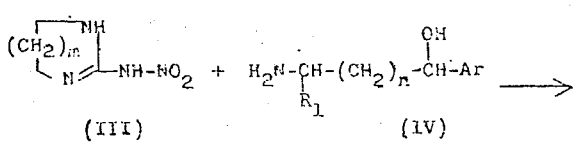

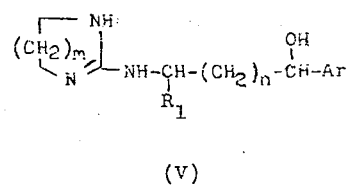

To prepare the compounds of formula (II), in which R is benzyl, an appropriate 2-benzylamino-imidazoline or 2-benzylamino-pyrimidine of formula (VI), wherein $m$ is zero or 1, is reacted with an appropriate aroyl alkyl halide, preferably the bromide, of formula (VII) wherein Ar and $n$ are as previously described, in a suitable organic solvent such as, for example, an aromatic hydrocarbon, e.g., benzene, toluene, xylene and the like, an ether, e.g., dioxane, diethyl ether, tetrahydrofuran and the like, and a lower alkanone, e.g., acetone, methyl ethyl ketone and the like. If desired, a stoichiometric excess of basic (VI) or a halogen acid scavenger may be added to pick up the halogen acid that is liberated during the course of the reaction. The carbonyl function of the thus-obtained condensation product (VIII) is reduced to a carbinol function (IX) by treatment with suitable reducing agents, such as sodium borohydride and the like. The foregoing reactions are illustrated as follows:

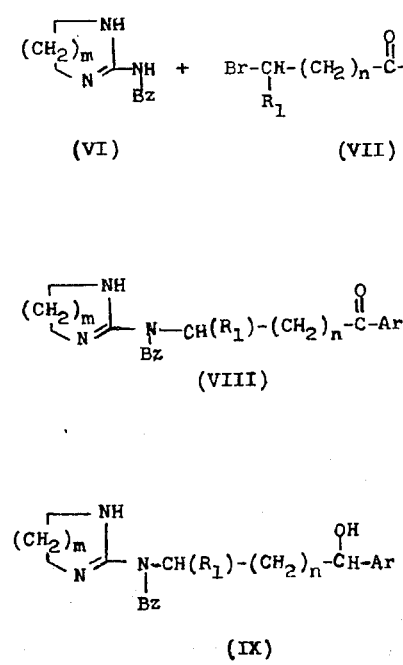

An alternative method of making the imidazo[1,2-a]-imidazolines and imidazo[1,2-a]pyrimidines of formula (I), wherein n is 0 and R=R$_1$=hydrogen, is through the following synthetic sequence. An appropriate nitrostyrene of formula (X), wherein Ar is as previously defined, is reacted with an appropriate aminoalkanol of formula (XI), wherein m is the integer zero or 1, in a suitable inert organic solvent and, preferably, in the cold (0°–5°C). The thusobtained nitro-alcohol base of formula (XII), which may be conveniently isolated by conventional transformation into an acid addition salt, for example, by treatment with alkanolic HCl, is then subjected to catalytic hydrogenation to afford the corresponding amino-alcohol of formula (XIII), which may also be similarly isolated in the form of an acid addition salt. The latter compound (XIII) is treated with carbon disulfide to thereby effectuate ring closure and yield the 2-thio-3-imidazolidine alkanol of formula (XIV). Transformation of the latter into the corresponding 2-methylthio-3-imidazoline alkanol of formula (XV) is accomplished by conventional methyl iodide treatment. The 2-methylthio function is transformed into a 2-amino function (XVI) by treatment with ammonia. The hydroxy function is replaced with a chloro function (XVII) by treatment with thionyl chloride, preferably at reflux temperatures in a suitable organic solvent such as, for example, chloroform. Ring closure into the desired bicyclic product (XVIII) is accomplished by treatment with alkali metal, e.g., sodium, in a suitable solvent, e.g., methanol, under reflux. The foregoing reaction sequence may be schematically illustrated as follows:

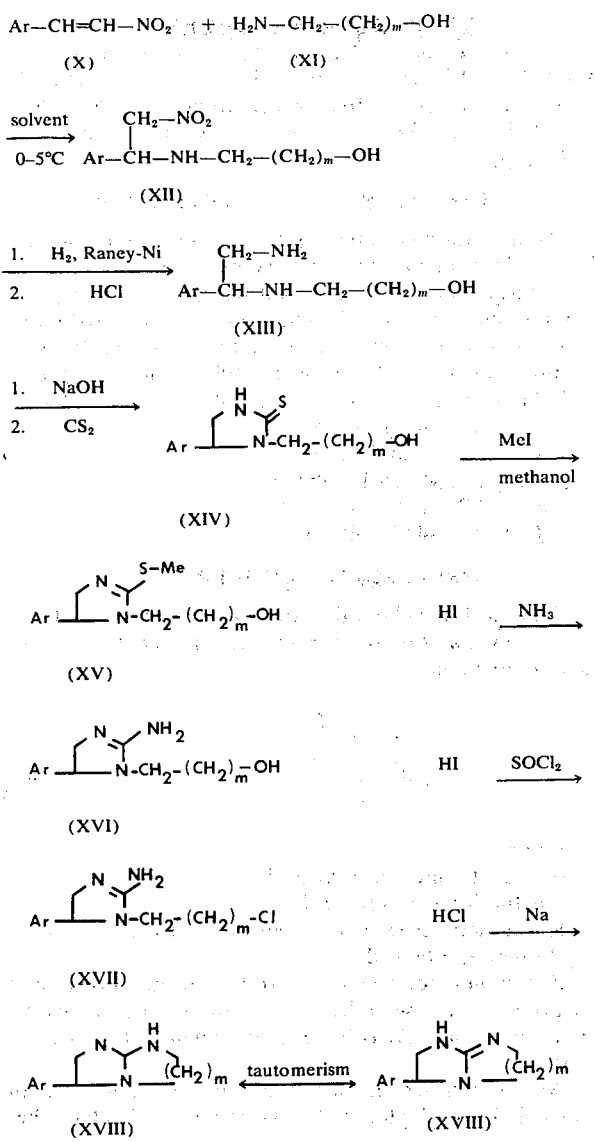

The subject compounds of formula (I) have been found to possess useful pharmacological properties as demonstrated in one or more of the following tests indicative of CNS antidepressant activity.

Test A. Amphetamine test in rats

An intravenous injection of 5 mg/kg of dextroamphetamine in rats induces pronounced CNS-stimulating effects that are characterized by stereotyped chewing movements, agitation and exophthalmia. These effects last for about 1 to 1½ hour after treatment. Pretreatment with antidepressants gives a prolongation of these typical effects which are still observable up to 4 hours after the injection of dextroamphetamine. The dose level at which the tested compound potentiates these effects of amphetamine is recorded.

Test B. Anti-tetrabenazine activity in mice

A subcutaneous injection of 10 mg/kg of Ro-4-1284 (a tetrabenazine-like compound) produces significant palpebral ptosis and hypothermia in mice. All known anti-depressants antagonize these effects when given before the challenging dose of Ro-4-1284. The lowest significant subcutaneous dose level at which the tested compound antagonizes the palpebral ptosis and the hypothermia, respectively, is recorded.

Test C. Test on vas deferens of the rat

A vas deferens is isolated and suspended in a 100 ml Tyrode-bath. Contractions are recorded on a Kymograph. Following a stabilization time of 15 minutes, noradrenaline is added to the bath-solution at 6-minutes intervals. The drug to be tested is added to the Tyrode-solution and the interaction with noradrenaline-induced contractions is measured. Drug effect is called potentiation if the noradrenalineinduced contraction obtained in the presence of the drug exceeds the response to noradrenaline previously obtained. The dose of the drug, expressed in mg per liter, which potentiates the noradrenaline respone is recorded.

In the following table, the CNS antidepresssant profile of several of he subject compounds is listed, as demonstrated by their relative responses to the aforementioned tests. It is understood that the compounds listed therein are not stated for purposes of limiting the invention thereto, but only to show the useful properties of all the compounds within the scope of formula (I).

TABLE 1

| Compound of Ex. No. | Amphet-amine-test - dose in mg/kg | Anti-tetrabenazine test antagonism of: | | Test on vas deferens mg/liter |
|---|---|---|---|---|
| | | palp.ptosis mg/kg | hypothermia mg/kg | |
| II | 2.5 | 0.16 | 0.08 | 0.0025 |
| III | 10 | 0.16 | 0.31 | 0.04 |
| IV | 10 | 0.31 | 0.31 | 0.01 |
| V | 2.5 | 0.16 | 0.63 | 0.16 |
| VI | 10 | 0.04 | 0.16 | 0.04 |
| VII | 10 | 0.63 | 0.63 | 0.01 |
| VIII | 10 | 0.63 | 0.63 | 0.01 |
| IX | — | 2.5 | 10 | 0.04 |
| X | 10 | 0.04 | 2.5 | 0.04 |
| XI | 10 | 10 | 10 | 0.04 |
| XII | 10 | 0.16 | 0.63 | 0.04 |
| XIII | 10 | 0.63 | 2.5 | 0.04 |
| XIV | — | 0.63 | 2.5 | 0.04 |
| XV-a | 2.5 | 0.16 | 0.31 | 0.0025 |
| XV-b | 10 | 2.5 | 2.5 | 0.04 | a = dextro isomer of Example I Compound
b = levo isomer of Example I Compound

Due to the assymetric carbons present in the subject compounds (I), it is evident that their existence in the form of stereochemical isomers (enantiomorphs) is possible. If desired, the resolution and isolation or the production of a particular form can be accomplished by application of general principles and techniques known in the art. Such pharmacologically active enantiomorphs are naturally intended to be included within the scope of this invention.

The organic bases of formula (I) may be converted to the corresponding pharmaceutically acceptable acid addition salts by reaction with an appropriate inorganic acid, such as, for example, hydrochloric, hydrobromic, hydriodic, sulfuric and the like acids, or with an appropriate organic acid, such as, for example, acetic, propionic, glycolic, lactic, oxalic, malonic, tartaric, citric, sulfamic, ascorbic and the like acids. In turn, the acid addition salts may be converted to the corresponding base form by conventional treatment with suitable alkali.

The preferred compounds herein are those of formula (I) in which m and n both equal zero, and R and $R_1$ both equal hydrogen, which compounds may be illustrated by the formula:

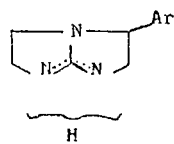

and denoted as 2,3,5,6-tetrahydro-3(5)-Ar-1H-imidazo[1,2-a]-imidazoles. The most preferred species are those in which Ar is phenyl and fluorophenyl.

The compounds of formula (II) and (VIII) are deemed to be novel and, in view of their utility as precursors in the synthetic procedures previously described, such compounds constitute an additional feature of this invention.

The following examples are intended to illustrate and not to limit the scope of the present invention. Unless otherwise stated, all parts are by weight.

EXAMPLE I

A mixture of 15.8 parts β-hydroxy-phenyl-amine, 13 parts 2-nitramino-2-imidazoline and 8 parts xylene is stirred and heated for 30 minutes at 160°C. (oil-bath). After cooling the reaction mixtures to a temperature of about 70°C., there are added 40 parts acetone. The whole is filtered warm and after cooling the filtrate to room temperature, the precipicated product is filtered off and dried, yielding 2-(β-hydroxy-phenethyl-amino)-2-imidazoline; m.p. 147°–149°C.

To 80 parts thionylchloride (previously cooled to 0°C.) are added 10.15 parts 2-(β-hydroxy-phenethyl-amino)-2-imidazoline. After the addition is complete, the whole is stirred for 30 minutes at room temperature and further stirred and refluxed for 15 minutes. The solvent is evaporated. The residue is dissolved in 40 parts toluene and evaporated again. This treatment is repeated by using 40 parts methanol. The residue is then dissolved in 40 parts 2-propanol. To this solution is added a solution of 1.15 parts sodium metal in 40 parts 2-propanol. The whole is stirred and refluxed for one hour. The solvent is evaporated. The residue is dissolved in 150parts water. The solution is filtered. The filtrate is alkalized with ammonium hydroxide and extracted three times with 40 parts ether and three times with 75 parts chloroform. The combined extracts are dried over potassium carbonate and evaporated. The solid residue is recrystallized from a mixture of 16 parts acetone and 16 parts 4-methyl-2-pentanone, yielding 2,3,5,6-tetrahydro-5-phenyl-1H-imidazo[1,2-a]imidazole; m.p. 167°–169.5°C.

EXAMPLE II

Three parts of 2-(β-hydroxyphenethylamino)-2-imidazoline are added portionwise to 11 parts of concentrated sulfuric acid solution at 0°C. The whole is stirred at room temperature for 2 hr. 30 minutes and poured onto crushed ice. The formed precipitate is filtered off and the filtrate is alkalized with sodium hydroxide. The product is extracted three times with chloroform (once with 75 parts and twice with 150 parts). The combined extracts are dried and evaporated. The residue is triturated in acetone, treated with activated charcoal, filtered and the filtrate is evaporated. The residue is converted into the hydrochloride salt in 4-methyl-2-pentanone. The precipitated salt is filtered off, washed with 2-propanol and dried, yielding 2,3,5,6-tetrahydro-5-phenyl-1H-imidazo[1,2-a]imidazole hydrochloride, m.p. 227.5°–229°C.

EXAMPLE III

A mixture pf 6.5 parts of α-(1-aminoethyl)benzyl alcohol (also known as morephedrine), 5.2 parts of 2-(nitramino)-2-imidazoline and 8 parts of xylene is stirred for 30 minutes while heating at 160°–170°C. The reaction mixture is cooled and diluted with acetone. The latter is removed in vacuo, yielding α-[1-(2-imidazolin-2-ylamino)-ethyl]benzyl alcohol as an oily residue.

A solution of 12 parts of the oily α-[1-(2imidazolin-2-ylamino)ethyl]benzyl alcohol in 40 parts of sulfuric acid solution 80% is stirred for 3 hours at room temperature. The reaction mixture is poured onto crushed ice. The whole is alkalized with sodium hydroxide solution and the product is extracted with toluene. The extract is dried, filtered and evaporated. The residue is washed with acetone and dried, yielding 2,3,5,6-tetrahydro-2-methyl-3-phenyl-1H-imidazo[1,2-a]imidazole; m.p. 179.4°C.

EXAMPLE IV

To a stirred solution of 8 parts of α(aminomethyl)-3,4-dichlorobenzyl alcohol in 4.5 parts of xylene are added 5.2 parts of 2-(nitramino)-2-imidazoline. The whole is heated in an oil-bath at a temperature of about 160°C. till a clear melt is obtained (about 15 minutes). After cooling to about 60°C., the melt is dissolved in acetone and allowed to crystallize. The precipitated product is filtered off and recrystallized from 20 parts of 4-methyl-2-pentanone, yielding 3,4-dichloro-α-(2-imidazolin 2-ylaminomethyl)benzyl alcohol; m.p. 148°C.

4.3 parts of 3,4-dichloro-α-(2-imidazolin-2-ylaminomethyl)benzyl alcohol are added portionwise to 16.2 parts of sulfuric acid solution 80% while stirring and cooling. Upon completion, the mixture is stirred for 2 hr. 30 min. at room temperature. The reaction mixture is poured onto ice-water, alkalized with concentrated sodium hydroxide solution and the product in base form is extracted with methylene chloride. The organic layer is dried, filtered and evaporated. The residue is converted into the hydrochloride salt in 2-propanol, yielding 5-(3,4-dichlorophenyl)-2,3,5,6-tetrahydro-1H-imidazo[1,2-a]imidazole hydrochloride; m.p. 298.4°C (dec.).

EXAMPLE V

To a solution of 6.5 parts of α-(aminomethyl)-p-fluorobenzyl alcohol in 8 parts of xylene are added 5.2 parts of 2-(nitramino)-2-imidazoline. The mixture is heated in an oil-bath to about 160°C. till gas-evolution is ceased (about 15 minutes). The reaction mixture is cooled and treated with benzene and acetone. The product is sucked off and crystallized from 4-methyl-2-pentanone, yielding p-fluoro-α-(2-imidazolin-2-ylaminomethyl)benzyl alcohol; m.p. 153.4°C.

To 18 parts of sulfuric acid 80% are added portionwise 2 parts of p-fluoro-α-(2-imidazolin-2-ylaminomethyl)-benzyl alcohol while cooling and stirring in an ice-bath. Upon completion, stirring is continued for 2 hr. 15 min. at room temperature. The reaction mixture is poured onto icewater, diluted with water till a volume of 150 parts, alkalized with concentrated sodium hydroxide solution and the product in base form is extracted with methylene chloride. The extract is dried and evaporated. The residue is converted into the hydrochloride salt, yielding 5-(p-fluorophenyl)-2,3,5,6-tetrahydro-1H-imidazo[1,2-a]imidazole hydrochloride; m.p. 259.8°C.

EXAMPLE VI

To 5.2 parts of 2-(nitramino)-2-imidazoline is added a solution of 7.5 parts of α-(aminomethyl)-p-chlorobenzyl alcohol in 40 parts of xylene while heating. Upon completion, stirring is continued while heating in an oil-bath at 150°–160°C. and while the xylene is partly distilled off (till gas evolution ceases). The residue is cooled and after the addition of a few parts of acetone, the produce is allowed to crystallize. It is filtered off, washed successively with acetone and diisopropylether, dried and the product is recrystallized from 4-methyl-2-pentanone, yielding p-chloro-α-(2-imidazolin-2-ylaminomethyl)benzyl alcohol; m.p. 156°–158°C.

3.4 parts of p-chloro-α-(2-imidazolin-2-ylaminomethyl)benzyl alcohol are added to 30 parts of sulfuric acid 80% while stirring and cooling in an ice-bath. Upon completion, the whole is stirred for 2 hours at room temperature. The reaction mixture is poured onto crushed ice, alkalized with a concentrated sodium hydroxide solution and the product in base form is extracted with methylene chloride. The extract is dried, filtered and evaporated. The residue is dissolved in 2-propanol. The solution is filtered over diatomaceous silica and the filtrate is acidified with an excess of 2-propanol previously saturated with gaseous hydrogen chloride. The precipitated salt is filtered off, washed with acetone and dried, yielding 5-(p-chlorophenyl)-2,3,5,6-tetrahydro-1H-imidazo[1,2-a]imidazole hydrochloride, m.p. 266.1°C.

EXAMPLE VII

A mixture of 8.2 parts of α-(aminomethyl)-m-methylbenzyl alcohol, 6.1 parts of 2-(nitramino)-2-imidazoline and 40 parts of xylene is stirred in an oil-bath at 150°–160°C, while almost all xylene is distilled off. The residue is diluted with a few parts of acetone and allowed to crystallize. The product is filtered off and recrystallized from 4-methyl-2-pentanone, yielding α-(2-imidazolin-2-ylaminomethyl)-m-methylbenzyl alcohol; m.p. 121°C.

4 parts of α-(2-imidazolin-2-ylaminomethyl)-m-methylbenzyl alcohol are added portionwise to 36 parts of sulfuric acid solution 80% while cooling in an ice-bath. The mixture is stirred for 2 hours at room temperature. The reaction mixture is poured onto crushed ice and the resulting solution is alkalized with sodium hydroxide solution at room temperature (cooling with ice is necessary). The product in base form is extracted with chloroform. The extract is converted into the hydrochloride salt in 2-propanol, yielding 2,3,5,6-tetrahydro-5-m-tolyl-1H-imidazo[1,2-α]imidazole hydrochloride; m.p. 269.1°C. (dec.).

EXAMPLE VIII

A mixture of 9.5 parts of α-(aminomethyl)-m-chlorobenzyl alcohol, 7.15 parts of 2-(nitramino)-2-imidazoline and 40 parts of xylene is stirred in an oil-bath at 150°–160°C. while a great part of the xylene is distilled off. The resulting residue is diluted with a few parts of acetone and the product is allowed to crystallize. It is filtered off and crystallized from 4-methyl-2-pentanone, yielding m-chloro-α-(2-imidazolin-2-ylaminomethyl)benzyl alcohol; m.p. 108.5°C.

4 parts of m-chloro-α-(2-imidazolin-2-ylaminomethyl)benzyl alcohol are added portionwise to 20 parts of cooled (ice-bath) sulfuric acid solution 80%. Upon completion, the whole is stirred for 2 hours at room temperature. The reaction mixture is poured onto crushed ice and the whole is filtered over diatomaceous silica. The filtrate is alkalized with ammonium hydroxide solution at room temperature (cooling is necessary) and the product in base form is extracted with chloroform. The latter is dried and evaporated. The residue is converted into the hydrochloride salt in 2-propanol, yielding 5-(m-chlorophenyl)-2,3,5,6-tetrahydro-1H-imidazo[1,2-a]imidazole hydrochloride; m.p. 249.8°C.

EXAMPLE IX

A mixture of 9.06 parts of α-(aminomethyl)-p-methylbenzyl alcohol, 7.8 parts of 2-(nitramino)-2-imidazoline and 8 parts of xylene is stirred for 30 minutes at 160°C (oil-bath). The reaction mixture is cooled and acetone is added. The precipitated product is filered off, washed with acetone and dried, yielding α-(2-imidazolin-2-ylaminomethyl)-p-methylbenzyl alcohol; 163.7°C.

A solution of 5 parts of α-(2-imidazolin-2-ylaminomethyl)-p-methylbenzyl alcohol in 45 parts of concentrated sulfuric acid is stirred overnight at room temperature. The reaction mixture is poured onto water, alkalized with sodium hydroxide and the product is extracted with toluene. The extract is dried and evaporated. The oily residue is stirred in acetone and the solid base product is filtered off. It is converted into the hydrochloride salt in 2-propanol, yielding 2,3,5,6-tetrahydro-3-p-tolyl-1H-imidazo-[1,2-a]imidazole hydrochloride; m.p. 254.2°C.

EXAMPLE X

A mixture of 7.2 parts of 1,4,5,6-tetrahydro-2-nitraminopyrimidine, 7.55 parts of α-(aminomethyl)-benzyl alcohol and 12 parts of xylene is stirred and refluxed for 4 hours on a water-tap. The xylene is evaporated and the residue is dissolved in 20 parts of acetone. The product is crystallized at room temperature. It is filtered off and dried, yielding α-(1,4,5,6-tetrahydro-2-pyrimidinylaminomethyl)benzyl alcohol.

4.4 parts of α-(1,4,5,6-tetrahydro-2-pyrimidinylaminomethyl)benzyl alcohol are stirred and cooled to 0°C. While keeping the temperature at 0°C, there are added portionwise 16.5 parts of sulfuric acid solution 80%. Upon completion, the whole is stirred for 2 hr. 30 minutes at room temperature. The reaction mixture is poured onto crushed ice, treated with activated charcoal, filtered and the filtrate is made strongly alkaline with 10N sodium hydroxide solution. The product is extracted with methylene chloride (three times 40 parts). The extract is dried and evaporated. The solid residue is treated with a small amount of acetone and the product in base form is filtered off again and converted into the hydrochloride salt of 2,3,5,6,7,8-hexahydro-3-phenylimidazo-[1,2-a]pyrimidine; m.p. 188°C.

EXAMPLE XI

To a stirred solution of 13.9 parts of 2,4'-dibromoacetophenone in 120 parts of acetone are added portionwise 8.75 parts of 2-(N-benzylamino)-2-imidazoline. Upon completion, stirring is continued for 2 days at room temperature. The precipitated product is filtered off, washed with acetone, dried and crystallized from ethanol, yielding 2-[N-benzyl-N-(2-imidazolin-2-yl)amino]-4'-bromoacetophenone hydrobromide, m.p. 262.9°C.

To a stirred suspension of 5.5 parts of 2-[N-benzyl-N-(2-imidazolin-2-yl)amino]-4'-bromoacetophenone hydrobromide in 80 parts of ethanol is added portionwise 0.45 parts of sodium borohydride at room temperature. Upon completion, stirring is continued overnight (about 16 hours). The reaction mixture is diluted with 50 parts of water and the ethanol is distilled off in vacuo. The residue is extracted with chloroform. The latter is dried and evaporated. The residue is converted into the hydrochloride salt in 2-propanol, yielding α-[N-benzyl-N-(2-imidazolin-2-yl)aminomethyl]-p-bromobenzylalcohol hydrochloride hemiisopropyl alcoholate, m.p. 148.4°C.

A mixture of 1.87 parts of α-[N-benzyl-N-(2-imidazolin-2-yl)aminomethyl]-p-bromobenzylalcohol and 27 parts of sulfuric acid 80% is stirred for 2 hours at room temperature. The reaction mixture is poured onto crushed ice. The whole is alkalized with sodium hydroxide solution and the product in base form is extracted with toluene. The latter is dried, filtered and evaporated. The residue is converted into the oxalate salt in 2-propanol. The crude salt is filtered off and crystallized from 2-propanol, yielding 1-benzyl-3-(p-bromophenyl)-2,3,5,6-tetrahydro-1H-imidazo[1,2-a]imidazole oxalate, m.p. 144.8°C.

EXAMPLE XII

A mixture of 8 parts of α-(2-aminoethyl)benzylalcohol, 6.5 parts of 2-(nitramino)-2-imidazoline and 40 parts of xylene is stirred and refluxed for 3 hours with waterseparator. The reaction mixture is cooled and the separated oily product is dissolved in 4-methyl-2-pentanone. The solvent is evaporated in vacuo, yielding α-{2-[N-(2-imidazolin-2-yl)amino]ethyl} benzylalcohol as a residue.

A mixture of 8 parts of α-{2-[N-(2-imidazolin-2-yl)amino]ethyl}benzylalcohol from the preceding step and 36 parts of sulfuric acid 80% is stirred for 3 hours at room temperature. The reaction mixture is poured onto crushed ice and the resulting solution is allowed to stand overnight at room temperature. It is then alkalized with sodium hydroxide solution and the product is extracted with toluene. The extract is dried, filtered and evaporated. The residue is triturated in acetone. The solid product is filtered off and crystallized from acetone, yielding 2,3,5,6,7,8-hexahydro-5-phenylimidazo[1,2-a]pyrimidine; m.p. 145.5°C.

EXAMPLE XIII

A mixture of 8 parts of α(2-aminoethyl)benzylalcohol, 7.2 parts of 2-(nitramino)-1,4,5,6-tetrahydropyrimidine and 40 parts of xylene is stirred and refluxed for 48 hours with waterseparator. Upon cooling the reaction mixture, the product is separated as an oil. The xylene is decanted and the oily product is triturated in diisopropylether. The solid product is filtered off and crystallized from acetone, yielding α-[2-(1,4,5,6-tetrahydro-2-pyrimidinylamino)ethyl]benzylalcohol; m.p. 130°-135°C.

A mixture of 2 parts of α-[2-(1,4,5,6-tetrahydro-2-pyrimidinylamino)ethyl]benzylalcohol and 27 parts of sulfuric acid 80% is stirred for 2 hours at room temperature. The reaction mixture is poured onto crushed ice and the whole is alkalized with sodium hydroxide solution. The product is extracted with toluene. The organic layer is separated, dried, filtered and evaporated. The solid residue is crystallized from acetone, yielding 3,4,6,7,8,9-hexahydro-6-phenyl-2H-pyrimido-[1,2-a]pyrimidine, m.p. 177°–179°C.

EXAMPLE XIV

A solution of 6.1 parts of 2-aminoethanol in 16 parts of methanol and 40 parts of ether is cooled on ice. Then there is added dropwise at about 5°C. a solution of 18.4 parts of o-chloro-α-nitrostyrene in 60 parts of ether. Upon completion, stirrng in an ice-bath is continued for 1 hour. The reaction mixture is acidified with an excess of 2-propanol previously saturated with gaseous hydrogen chloride. The precipitated product is filtered off, washed thoroughly with ether and dried, yielding 2-{N-[o-chloro-α-(nitromethyl)benzyl]amino}ethanol hydrochloride.

To a mixture of 26 parts of 2-{N-[o-chloro-α-(nitromethyl)benzylamino}ethanol hydrochloride and 2 parts of Raney-Nickel catalyst is added 120 parts of methanol (cooled in a mixture of methanol/carbon dioxide), followed by the addition of 20 parts of carbon dioxide. The whole is hydrogenated at 50 lbs/sq. inch pressure over 2 hours. The catalyst is filtered off and the filtrate is acidified with an excess of 2-propanol previously saturated with gaseous hydrogen chloride. The precipitated salt is filtered off, washed with methanol and dried, yielding 2-{N-[α-(aminomethyl)-o-chlorobenzyl]amino}ethanol dihydrochloride.

To a stirred mixture of 5.75 parts of 2-{N-[α-(aminomethyl)-o-chlorobenzyl]amino}ethanol dihydrochloride, 8 parts of ethanol and 6 parts of water is added 4 parts of sodium hydroxide solution 10N. To the resulting clear solution are added dropwise 1.68 parts of carbon disulfide and the whole is stirred and refluxed for 1 hour. After the addition of 0.2 parts of hydrochloric acid solution 10N, stirring and refluxing is continued for 5 hours. The reaction mixture is cooled to room temperature and the precipitated product is filtered off. It is washed successively with a mixture of water and ethanol (1:1 by volume), with ethanol and with water, and dried. The product is crystallized from ethanol, yielding 4-(o-chlorophenyl)-2-thio-3-imidazolidineethanol; m.p. 169.1°C.

A mixture of 12.84 parts of 4-(o-chlorophenyl)-2-thio-3-imidazolidineethanol, 7.81 parts of methyl iodide and 40 parts of methanol is stirred for 4 hours at 40°C. Diispropylether is added and the solvent is decanted, yielding 5-(o-chlorophenyl)-2-(methylthio)-2-imidazoline-1-ethanol hydroiodide as an oily residue.

A mixture of 18.3 parts of 5-(o-chlorophenyl)-2-(methylthio)-2-imidazoline-1-ethanol hydroiodide and 40 parts of methanol saturated with ammonia is stirred and refluxed for 2 hours. The solvent is evaporated and the solid residue is treated with 20 parts of 2-propanol. The product is filtered off and recrystallized from 50 parts of water, yielding 2-amino-5-(o-chlorophenyl)-2-imidazoline-1-ethanol hydroiodide, m.p. 181.6°C.

A mixture of 4.15 parts of 2-amino-5-(o-chlorophenyl)-2-imidazoline-1-ethanol hydrochloride in 22.5 parts of chloroform is treated with 3.6 parts of thionyl chloride and the whole is stirred at reflux temperature for 30 minutes. The solvent is evaporated and the residue is taken up in 15 parts of chloroform. The latter is evaporated again, yielding 2-amino-1-(2-chloroethyl)-5-(o-chlorophenyl)-2-imidazoline hydrochloride as a residue.

To a stirred solution of 4.6 parts of 2-amino-1-(2-chloroethyl)-5-(o-chlorophenyl)-2-imidazoline hydrochloride in 12 parts of methanol is added a solution of 0.725 parts of sodium in 12 parts of methanol. The whole is stirred and refluxed for 1 hr. 30 minutes. The reaction mixture is evaporated and to the residue is added 50 parts of water and a small amount of a 10N sodium hydroxide solution. The product is extracted twice with 40 parts of methylene chloride. The combined extracts are dried, filtered and evaporated. The residue is converted into the hydrochloride salt in 2-propanol and diisopropylether. The salt is filtered off, washed with acetone and dried, yielding 5-(o-chlorophenyl)-2,3,5,6-tetrahydro-1H-imidazo[1,2-a]imidazole hydrochloride; m.p. 215°–222°C.

EXAMPLE XV

To a stirred solution of 10.7 parts of (±)-2,3,5,6-tetrahydro-5-phenyl-1H-imidazo[1,2-a]imidazole in 20 parts of methanol is added a warm solution of 8.6 parts of (+)-tartaric acid in 20 parts of methanol. The whole is diluted with 80 parts of acetone and the product is allowed to crystallize. The precipitated fraction is filtered off [about 5.6 parts of crude (+)-2,3,5,6-tetrahydro-5-phenyl-1H-imidazo[1,2-a]-imidazole (+)-tartrate - α(1% MeOH): +87.3°]and set aside. The filtrate is evaporated in vacuo. The residue is dissolved in water and the free base is liberated. It is extracted with chloroform and the latter is dried and evaporated. The residue is dissolved in 28 parts of methanol and to this solution is added a warm solution of 5.7 parts of (−)-tartaric acid in 60 parts of methanol. The product is allowed to crystallize. It is filtered off and recrystallized from a mixture of 8 parts of methanol and 16 parts of acetone till a constant rotation, yielding about 4.3 parts of (−)-2,3,5,6-tetrahydro-5-phenyl-1H-imidazo[1,2-a]imidazole(−)-tartrate; α(1% MeOH): −89.97°. A sample of 4.2 parts of (−)-2,3,5,6-tetrahydro-5-phenyl-1H-imidazo[1,2-a]imidazole(−)-tartrate is dissolved in water and the free base is liberated. After extraction with chloroform, the latter is dried and evaporated. The residue is crystallized from acetone, yielding about 0.7 parts of (−)-2,3,5,6-tetrahydro-5-phenyl-1H-imidazo[1,2-a]-imidazole; m.p. 153.2°C.; α(1% MeOH): −211.49°. The free base together with the residue of the evaporated mother-liquor is converted into the hydrochloride salt yielding about 1.9 parts of (−)-2,3,5,6-tetrahydro-5phenyl-1H-imidazo[1,2-a]-imidazole hydrochloride; m.p. 277.1°C.; α(1% MeOH): −115.79°.

The first precipitated product of about 5.6 parts which was set aside is crystallized from a mixture of 8 parts of methanol and 16 parts of acetone till constant rotation, yielding about 3.5 parts of (±)-2,3,5,6-tetrahydro-5-phenyl-1H-imidazo[1,2-a]imidazole (±)-tartrate, a (1% MeOH): +88.83°, is dissolved in water and the free base is liberated. After extraction with chloroform, the latter is dried and evaporated. The residue is crystallized from acetone, yielding about 1 part of (+)-2,3,5,6-tetrahydro-5-phenyl-1H-imidazo[1,2-a]imidazole; m.p. 152.6°C.; α(1% MeOH): +214.41°. The free base together with the residue of the evaporated mother-liquor is converted into the hydrochloride salt in 2-propanol, yielding about 1.5 parts of (+)-2,3,5,6-tetrahydro-5-phenyl-1H- imidazo[1,2-a]imidazole hydrochloride; m.p. 277.3°C.; α(1% MeOH): +114.42°.

EXAMPLE XVI

The procedure of Example X may be followed to prepare the 2,3,5,6,7,8-hexahydro-3-Ar-imidazo[1,2-a]pyrimidines of formula (I). For example, by substituting an equivalent quantity of the 4—Br—, 4—Me—, 4—Et—, 3,4,—di—Cl— derivative of α-(aminomethyl)benzyl alcohol for the ring-unsubstituted benzyl alcohol used therein, the following respective products are obtained:

3-(4-bromophenyl)-2,3,5,6,7,8-hexahydro-imidazo[1,2-a]-pyrimidine;

2,3,5,6,7,8-hexahydro-3-(4-methylphenyl)-imidazo[1,2-a]-pyrimidine;

3-(4-ethylphenyl)-2,3,5,6,7,8-hexahydro-imidazo[1,2-a]-pyrimidine; and 3-(3,4-dichlorophenyl)-2,3,5,6,7,8-hexahydro-imidazo-[1,2-a]pyrimidine.

EXAMPLE XVII

The procedure of Example XI may be followed to prepare the compounds of formula (I) wherein R is benzyl. For example, by utilizing as starting materials a respective equivalent amount each of an appropriate compound of formulas (VI) and (VII), the following respective products are obtained in the form of an oxalate salt:

1-benzyl-3-(p-methylphenyl)-2,3,5,6-tetrahydro-1H-imidazo[1,2-a]imidazole;

1-benzyl-3-(3,4-dichlorophenyl)-2,3,5,6-tetrahydro-1H-imidazo[1,2-a]imidazole;

1-benzyl-3-(p-bromophenyl)-2,3,5,6,7,8-hexahydro-1H-imidazo[1,2-a]pyrimidine;

1-benzyl-3-phenyl-2,3,5,6,7,8-hexahydro-1H-imidazo-[1,2-a]pyrimidine; and 1-benzyl-3,4,6,7,8,9-hexahydro-6-phenyl-2H-pyrimido-[1,2-a]pyrimidine.

EXAMPLE XVIII

The procedure of Example XII may be followed to prepare the 2,3,5,6,7,8-hexahydro-5-Ar-imidazo-[1,2-a]pyrimidines of formula (I). For example, by substituting an equivalent amount of the 4—Cl—, 4—Me— and 3,4-di—Cl derivatives of α-(2-aminoethyl)benzyl alcohol for the ring-unsubstituted benzyl alcohol used therein, the following respective products are obtained:

5(4-chlorophenyl)-2,3,5,6,7,8-hexahydro-imidazo-[1,2-a]pyrimidine;

2,3,5,6,7,8-hexahydro-5-(4-methylphenyl)-imidazo-[1,2-a]pyrimidine; and 5-(3,4-dichlorophenyl)-2,3,5,6,7,8-hexahydro-imidazo-[1,2-a]pyrimidine.

EXAMPLE XIX

The procedure of Example XIII may be followed to prepare the 3,4,6,7,8,9-hexahydro-6-Ar-2H-pyrimido-[1,2-a]pyrimidines of formula (I). For example, by substituting an equivalent amount of the 4—Br—, 4—Me—, and 3,4—di—Cl—derivatives of α-(2-aminoethyl)benzyl alcohol for the ring-unsubstituted benzyl alcohol used therein, the following respective products are obtained:

6-(4-bromophenyl)-3,4,6,7,8,9-hexahydro-2H-pyrimido-[1,2-a]pyrimidine;

3,4,6,7,8,9-hexahydro-6-(4-methylphenyl)-2H-pyrimido-[1,2-a]pyrimidine; and 6-(3,4-dichlorophenyl)-3,4,6,7,8,9-hexahydro-2H-pyrimido[1,2-a]pyrimidine.

We claim:

1. A chemical compound having the formula:

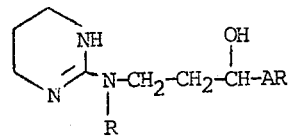

wherein:

R is a member selected from the group consisting of hydrogen and benzyl; and

Ar is a member selected from the group consisting of phenyl, loweralkylphenyl, halophenyl and dihalophenyl.

2. A chemical compound having the formula:

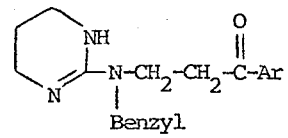

wherein:

Ar is a member selected from the group consisting of phenyl, loweralkylphenyl, halophenyl and dihalophenyl.

* * * * *

UNITED STATES PATENT AND TRADEMARK OFFICE
CERTIFICATE OF CORRECTION

PATENT NO. : 3,963,718
DATED : June 15, 1976
INVENTOR(S) : Van Gelder et al.

It is certified that error appears in the above-identified patent and that said Letters Patent are hereby corrected as shown below:

In Column 1, line 40, "when" should read ---then---
In Column 1, line 54, " iodö" should read ---iodo.---
In Column 5, line 18, "respone" should read ---response---
In Column 5, line 19, "he" should read ---the---
In Column 6, line, 45, "150parts" should read ---150 parts---
In Column 7, line 6, "pf" should read ---of---
In Column 8, line 15, "produce" should read ---product---
In Column 9, line 22, "filered" should read ---filtered---
In Column 10, line 55, "a(2-aminoethyl)" should read "a-(2-aminoethyl)"
In Column 11, line 13, "stirrng" should read ---stirring---
In Column 12, line 57, "($\pm$)" should read ---(+)---
In Column 12, line 58, "(+)" should read ---($\pm$)---

*Signed and Sealed this*

*Fourteenth* Day of *February 1978*

[SEAL]

Attest:

RUTH C. MASON
*Attesting Officer*

LUTRELLE F. PARKER
*Acting Commissioner of Patents and Trademarks*